United States Patent
Noda

(10) Patent No.: US 10,258,339 B2
(45) Date of Patent: Apr. 16, 2019

(54) DEVICES AND METHODS FOR SECURING TISSUE

(71) Applicant: Insightra Medical, Inc., Clarksville, TN (US)

(72) Inventor: Wayne A. Noda, Mission Viejo, CA (US)

(73) Assignee: Insightra Medical, Inc., Clarksville, TN (US)

( * ) Notice: Subject to any disclaimer, the term of this patent is extended or adjusted under 35 U.S.C. 154(b) by 0 days.

(21) Appl. No.: 14/714,730

(22) Filed: May 18, 2015

(65) Prior Publication Data

US 2015/0305747 A1    Oct. 29, 2015

Related U.S. Application Data

(60) Division of application No. 13/477,649, filed on May 22, 2012, now Pat. No. 9,125,656, and a
(Continued)

(51) Int. Cl.
*A61B 17/12* (2006.01)
*A61B 17/064* (2006.01)
(Continued)

(52) U.S. Cl.
CPC .. *A61B 17/12013* (2013.01); *A61B 17/00234* (2013.01); *A61B 2017/00349* (2013.01);
(Continued)

(58) Field of Classification Search
CPC ...... A61B 17/12013; A61B 2017/0641; A61B 2017/12018; A61B 2017/00349
(Continued)

(56) References Cited

U.S. PATENT DOCUMENTS

| 4,517,090 A | 5/1985 | Kersten et al. |
| 4,548,201 A * | 10/1985 | Yoon .................. A61F 6/202 |
| | | 128/831 |

(Continued)

FOREIGN PATENT DOCUMENTS

| WO | 1996025886 A9 | 10/1996 |
| WO | 1996029965 A1 | 10/1996 |

OTHER PUBLICATIONS

"6 Shooter Universal Saeed Multi-Band Ligator", Cook Medical, Retrived on Aug. 1, 2015 from https://www.cookmedical.com/products/esc_mbl_webds/.
(Continued)

*Primary Examiner* — Vy Q Bui
(74) *Attorney, Agent, or Firm* — Sullivan & Worcester LLP

(57) ABSTRACT

A compression ring to grip and compress body structure such as diverticulum, hemorrhoids, and tissue adjacent a hole. A resilient ring-shaped body defines a compression channel, and an elongated axially rigid gripping member extends diametrically across the through-opening. The gripping member can rest on a flange on the opposite side of the through-opening or engage with a second gripping member that extends diametrically across the through-opening from the opposite side of the ring. Or, a flexible cage structure can be disposed in the through-opening.

2 Claims, 12 Drawing Sheets

Related U.S. Application Data continuation-in-part of application No. 13/240,018, filed on Sep. 22, 2011, now abandoned, which is a continuation of application No. 12/141,391, filed on Jun. 18, 2008, now Pat. No. 8,062,308.

(60) Provisional application No. 61/492,289, filed on Jun. 1, 2011, provisional application No. 61/012,124, filed on Dec. 7, 2007, provisional application No. 60/982,083, filed on Oct. 23, 2007.

(51) Int. Cl.
*A61B 17/00* (2006.01)
*A61B 17/30* (2006.01)

(52) U.S. Cl.
CPC ............ *A61B 2017/00526* (2013.01); *A61B 2017/00893* (2013.01); *A61B 2017/0641* (2013.01); *A61B 2017/12018* (2013.01); *A61B 2017/306* (2013.01)

(58) Field of Classification Search
USPC .............................. 606/139, 140, 141, 206
See application file for complete search history.

(56) References Cited

U.S. PATENT DOCUMENTS

| | | | |
|---|---|---|---|
| 4,820,304 A | | 4/1989 | Depel et al. |
| 5,741,273 A | * | 4/1998 | O'Regan .......... A61B 17/12013 606/1 |
| 5,972,009 A | | 10/1999 | Fortier et al. |
| 5,976,158 A | | 11/1999 | Adams et al. |
| 5,980,537 A | | 11/1999 | Ouchi |
| 6,849,078 B2 | | 2/2005 | Durgin et al. |
| 7,189,247 B1 | | 3/2007 | Zirps et al. |
| 7,641,652 B2 | | 1/2010 | Coe et al. |
| 7,766,020 B2 | | 8/2010 | Chininis et al. |
| 7,819,895 B2 | | 10/2010 | Ginn et al. |
| 8,062,308 B2 | | 11/2011 | Noda et al. |
| 8,647,352 B2 | | 2/2014 | Noda et al. |
| 2005/0192629 A1 | | 9/2005 | Saadat et al. |
| 2007/0225762 A1 | | 9/2007 | LaBombard |
| 2009/0105728 A1 | | 4/2009 | Noda et al. |
| 2009/0157101 A1 | | 6/2009 | Reyes et al. |

OTHER PUBLICATIONS

Wayne A. Noda, "Devices and Methods for Securing Tissue", file history of related U.S. Appl. No. 13/477,649, filed May 22, 2012.
Wayne A. Noda, "Delivery Assembly for Resilient Tissue Clamp", file history of related U.S. Appl. No. 13/898,896, filed May 21, 2013.
Wayne A. Noda, Stephen Graham Bell, "Devices and Methods for Securing Tissue", file history of related U.S. Appl. No. 14/043,038, filed Oct. 1, 2013.
Wayne A. Noda, Stephen Graham Bell, "Devices and Methods for Securing Tissue", related U.S. Appl. No. 14/043,038, Non-Final Office Action dated Apr. 11, 2016.
Wayne A. Noda, Stephen Graham Bell, "Devices and Methods for Securing Tissue", related U.S. Appl. No. 14/043,038, Applicant's response to Non-Final Office Action filed Apr. 12, 2016.

\* cited by examiner

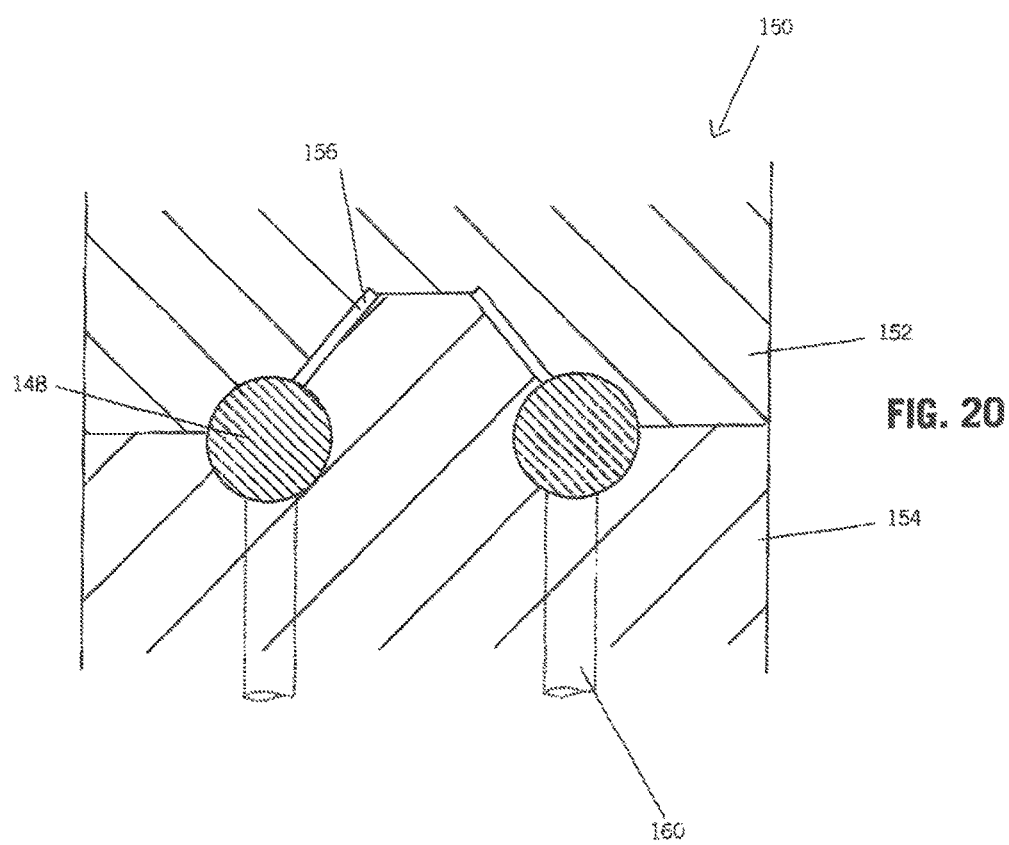

DEVICES AND METHODS FOR SECURING TISSUE

This application claims priority to U.S. provisional patent application 61/492,289, filed Jun. 1, 2011 and incorporated herein by reference. This application is also a continuation in part of U.S. patent application Ser. No. 13/240,018, filed Sep. 22, 2011, which is a continuation of U.S. patent application Ser. No. 12/141,391, filed Jun. 18, 2008, now U.S. Pat. No. 8,062,308, which in turn claims priority from U.S. provisional patent applications Ser. Nos. 60/982,083, filed Oct. 23, 2007 and 61/012,124, filed Dec. 7, 2007. Priority is claimed to all of the above documents. U.S. Pat. No. 8,062,308 is incorporated herein by reference.

FIELD OF THE INVENTION

The present application relates generally to devices and methods for securing tissue.

BACKGROUND

Internal body tissue sometimes must be secured together for various reasons. As an example, diverticulosis is an unfortunately common condition in which an area of the intestine bulges out into the peritoneal cavity to form a sac referred to as a "diverticulum". The above-referenced patent envisions a natural orifice method for resolving diverticulum by inverting them and then securing opposed serosal surfaces together using a ring to thereby tightly and securely close off the affected tissue to alleviate the risk of peritonitis.

While the patented approach is effective, present principles further understand that slippage of the ring can occur once it is placed on tissue. In the colon and bowel, for instance, significant peristalsis and pressure can stretch the tissue wall, which can force the ring off the tissue, losing the therapeutic effect of the ring.

SUMMARY OF THE INVENTION

A ring for engaging tissue has a round resilient body defining an axial through-opening configured to receive the tissue. At least one elongated axially rigid gripping member extends diametrically across the through-opening. The gripping member has a first end embedded in the ring and a second end distanced from the first end and not embedded in the ring. The gripping member extends substantially entirely across the through-opening.

In one implementation, the gripping member rests on a flange attached to a portion of the through-opening opposite to where the gripping member is embedded in the ring. In another example, the gripping member is first gripping member and the ring includes a second gripping member that extends diametrically across the through-opening from a portion of the ring opposite to where the gripping member is embedded in the ring. Each gripping member may be barbed in that each gripping member may be formed with a respective barb extending away from the other gripping member. Or, the first gripping member can be flat and can include a hook segment forming a bight, while the second gripping member can define a long axis and can be twisted about the long axis. The second gripping member likewise includes a hook forming a bight, and the bights of the gripping members face each other.

Yet again, in another embodiment the first gripping member is urgable by tissue through an eye formed in the second gripping member. Or, the first gripping member can be wider than the second gripping member, with the gripping members being flushly disposed with each other throughout their length. In this last embodiment, first and second stabilizing elements can be formed on the ring in an orthogonal relationship to the gripping members, extending into the through-opening.

In another aspect, a ring for engaging tissue includes a round resilient body defining an axial through-opening configured to receive the tissue, and a flexible cage structure disposed in the through-opening.

In another aspect, a method for making a tissue gripping ring includes forming at least one spike on a circular support, with the spike extending inward relative to the circular support. The method includes overmolding a toroidal resilient ring onto the spike, removing the spike and ring from the circular support, and removing excess ring material from the spike.

In another aspect, a method for configuring a resilient ring for placement in a patient to cause the ring to surroundingly grip tissue in the patient includes engaging the ring with a first end of an expander. The expander tapers radially outwardly from the first end to a cylindrical segment, with a diameter of the first end substantially equaling a diameter of the ring when the ring is in a relaxed state. The method contemplates pushing the ring along the expander to radially stretch fee ring until the ring surrounds the cylindrical segment. The cylindrical segment is juxtaposed with a carrying portion of a delivery device having substantially the same diameter as the cylindrical segment, and then the ring is pushed from the cylindrical segment onto the carrying portion to load the ring in a stretched state for delivery to the tissue.

The details of the present invention, both as to its structure and operation, can best be understood in reference to the accompanying drawings, in which like reference numerals refer to like parts, and in which:

BRIEF DESCRIPTION OF THE DRAWINGS

FIG. 20 is a cross-sectional view showing an example mold with an example ring therein to further illustrate methods for making the ring.

DETAILED DESCRIPTION OF THE PREFERRED EMBODIMENT

Figure 1:
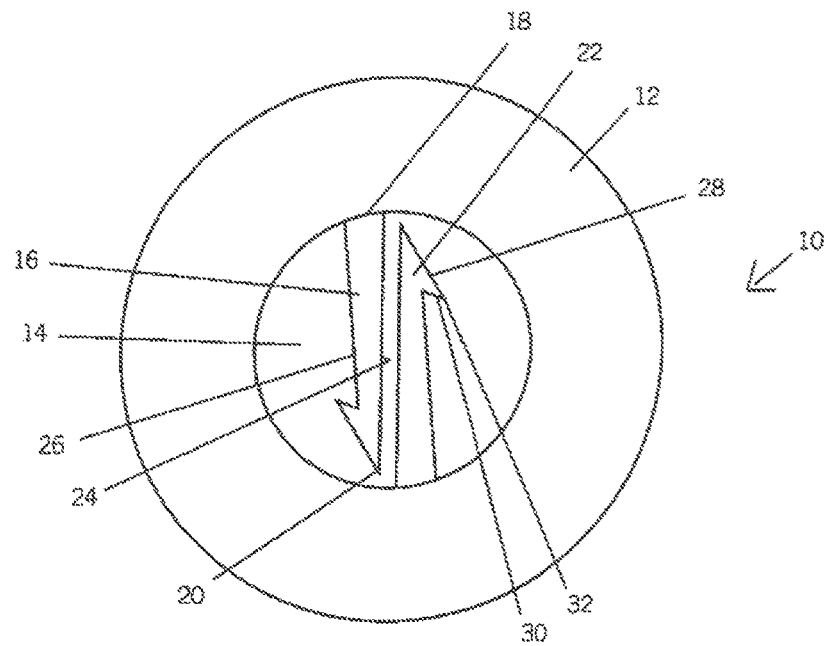
FIG. 1 is a top plan view of a first embodiment of the present tissue ring.

Referring initially to FIG. 1, a ring is shown, generally designated 10, which includes a disk-shaped or more preferably toroidal body 12 made of resilient material such as silicone or other biocompatible resilient material. Note that in general, the body is round with a central opening, although non-limiting examples below disclose toroidal bodies. In the relaxed state shown, the ring 10 assumes a radially smaller configuration, and is resilient so that it can be stretched to a radially enlarged state to fit onto a delivery device as explained further below. The ring is slid off the delivery device to engage tissue such as but not limited to a diverticulum to surround and compress the tissue. In the case of an inverted diverticulum as disclosed in the above-referenced patent, it is compressed by the ring 10 in its inverted state, and so is closed off serosa to serosa.

As shown in FIG. 1, the ring 10 also includes a spike design having a barb element to prevent backing out of the tissue once it has been installed. With more specificity, the body 12 defines an axial through-opening 14 configured to receive the tissue, and one or more (in the embodiment shown, two) elongated axially rigid gripping members 16 which may be configured as spikes as shown in the example extend diametrically across the through-opening, parallel to each other and side by side, i.e., are offset from each other in the radial dimension defined by the body. In one example embodiment, the gripping members are made of stainless steel.

As shown, each gripping member 16 has a respective first end 18 embedded in the ring and a second end 20 distanced from the first end and not embedded in the ring. In the example shown, the second end 20, which is a free end, is pointed, and extends almost to the body 12 but does not quite reach the body 12, thus extending substantially entirely across the through-opening 14. In some examples, each gripping member 16 extends at least past the longitudinal axis defined by the body 12, and preferably extends to eighty percent (80%) of the way across the diameter of the through-opening 14. More preferably still, each gripping member 16 extends to at least ninety percent (90%) of the way across the diameter of the through-opening 14.

In the example of FIG. 1, each gripping member 16 is barbed, in that each gripping member is formed with a respective barb 22 extending away from the other gripping member. Specifically describing an example barb, each gripping member 16 may have a straight inside edge 24 and an opposed outside edge 26, and the barb 22 is established by an extension at the second end 20 of the gripping member 16 that has two opposed barb surfaces 28, 30 extending outwardly away from the outside edge 26 at an acute angle thereto and tapering to a barb point 32. The inside edges 24 of the gripping members face each other as shown.

Figure 2:
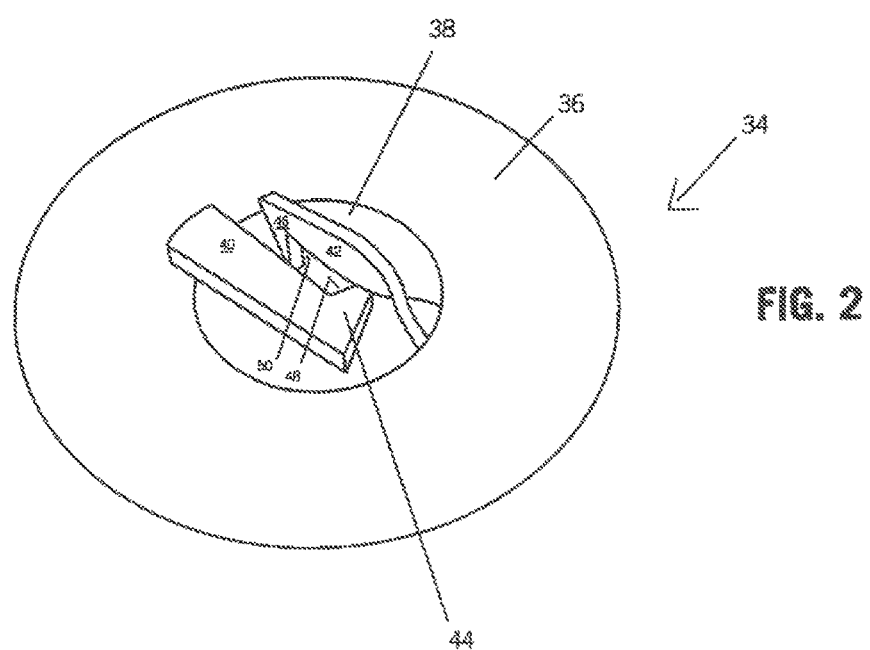
FIG. 2 is a perspective view of a second embodiment of the present tissue ring.

Turning to FIG. 2, barbed spikes are shown wherein the barb structures engage with each other and lock together. With greater specificity, a ring 34 with a toroidal ring body 36 defines a through-opening 38, and first and second gripping members 40, 42 extend diametrically across the opening 38 side by side. i.e., are offset from each other in the radial dimension defined by the body. The gripping members 40, 42 are formed at their respective free ends with respective hook segments 44, 46, each forming, in concert with the rest of the gripping member, a respective bight 48, 50. The first gripping member 40 is flat as shown, whereas the second gripping member defines a long axis and is twisted about the long axis. The bights 48, 50 of the gripping members 40, 42 face each other so that as tissue forces the gripping members 40, 42 together, the hook segments engage with each other and under the force of the tissue lock together.

Figure 3A:
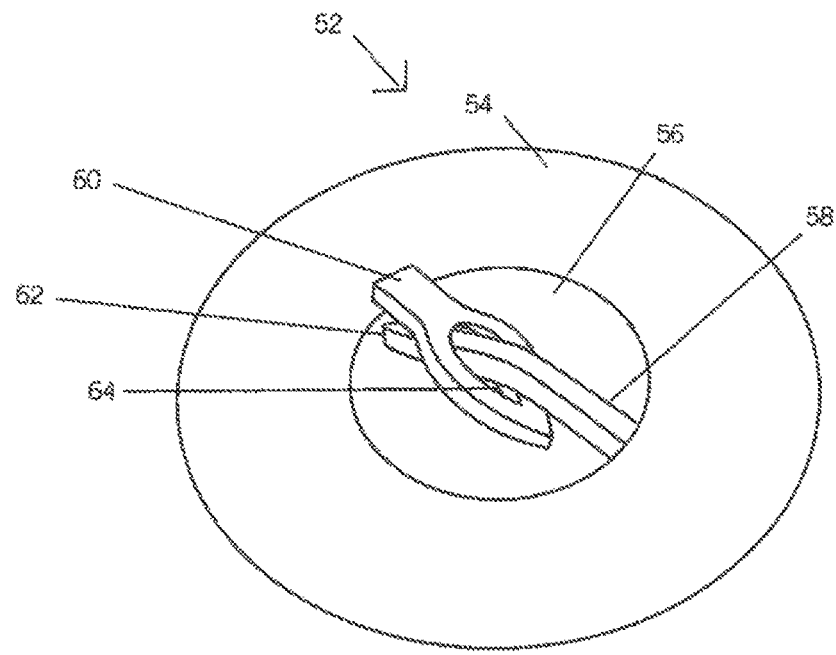
FIG. 3A is a perspective view of a third embodiment of the present tissue ring.
Figure 3B:
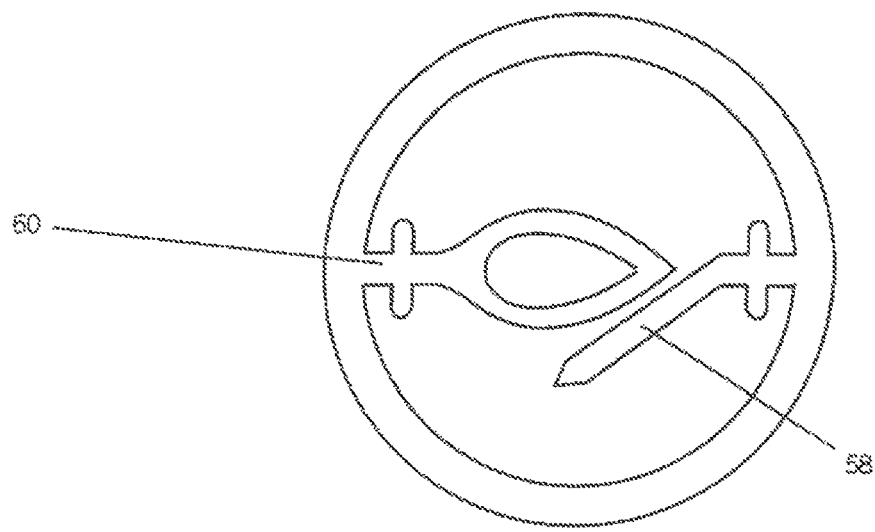
FIG. 3B is a top plan view of the third embodiment of the present tissue ring showing an intermediate configuration of the gripping members during manufacture.

Now considering FIGS. 3A and 3B, a spike design is shown with a nesting configuration. As will be explained shortly in further detail, one gripping member establishes a prong like structure and the opposite gripping member has a receptacle structure designed for receiving the opposing member. When the ring is applied to tissue, the ring is first stretched and the spikes rotated out parallel to the central axis of the ring. When released onto the tissue, the spikes spontaneously rotate inwards to the resting position of the molded elastomeric material. The ring eventually compresses to the tightest diameter possible and while doing so, the spikes engage and interlock with themselves. Once interlocked, there is not adequate expansion force from the tissue to enlarge the ring that would allow the spikes to release and slip off of the tissue. These spike designs take advantage of the ring having to be stretched open prior to applying to the tissue. Once released, the spikes become locked together and the only way to unlock them is to reexpand the ring, which is not feasible once implanted into the body.

In greater detail, a ring 52 with a toroidal ring body 54 defines a through-opening 56, and first and second gripping members 58, 60 extend diametrically across the opening 56 side by side, i.e., are offset from each other in the radial dimension defined by the body. The first gripping member 58 terminates in a distal point 62 as shown, and the first gripping member can be urged by tissue through an eye 64 formal in the second gripping member 60. As shown, in FIG. 3, the first gripping member 58 is formed offset from the diameter of the ring and is straightened after molding the body 54 onto the gripping members to a configuration in which the first gripping member extends diametrically across the through-opening 56 so that it can slide into the eye 64 when so urged by tissue.

FIGS. 4-9 illustrate various facets of yet another embodiment in which a spike design is shown with an overlapping configuration. The two overlapping spikes discussed further below prevent each other from rotating outwards. For the outer spike to rotate inwards, the inner spike must fully rotate inwards to clear the tip of the outer spike in a sequential manner, and since this is not how tissue entrapped on the spikes will cause the spikes to react since the outer spike tip does not have enough force acting on the inner spike to rotate it out of the way, the outer spike remains anchored across the diameter. If the outer spike cannot move, then the inner cannot move and clear first, thereby establishing an interlocking feature in which each spike lying across the diameter effectively fights each other from movement and slippage.

Figure 4:
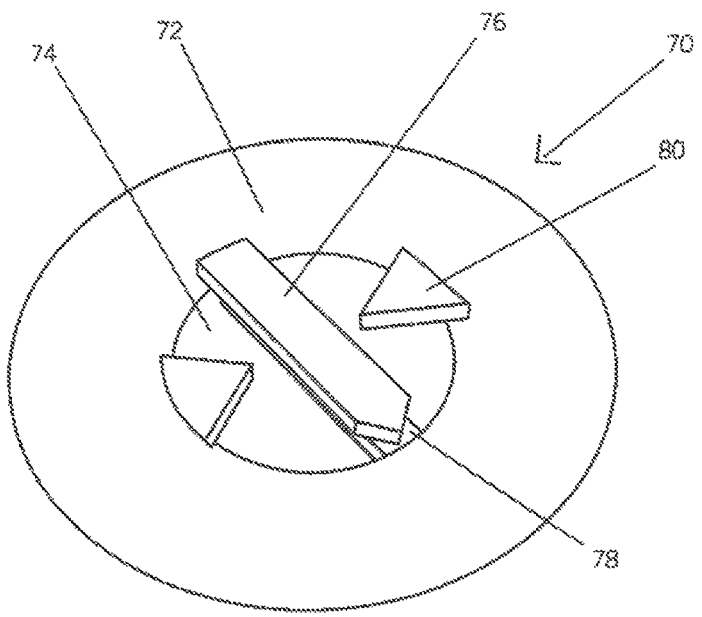
FIGS. 4-9 are various views of a fourth embodiment of the ring and stages of installing it in a patient.
Figure 5:
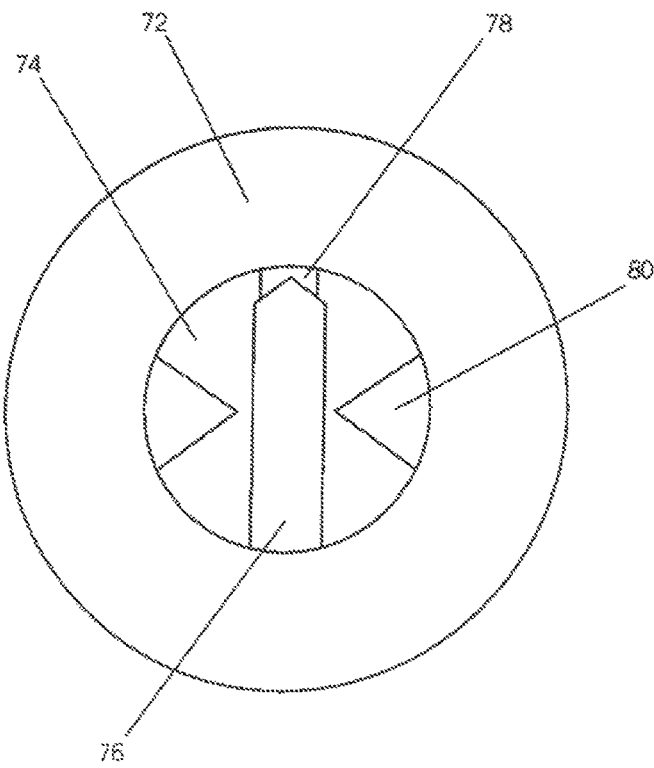
Figure 6:
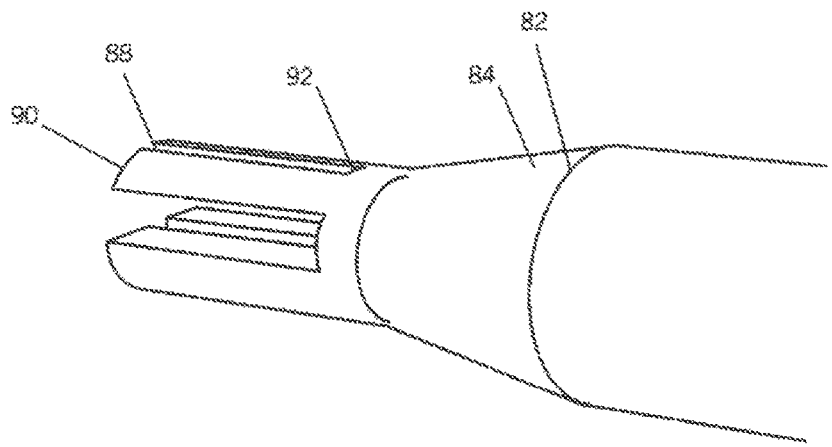
Figure 7:
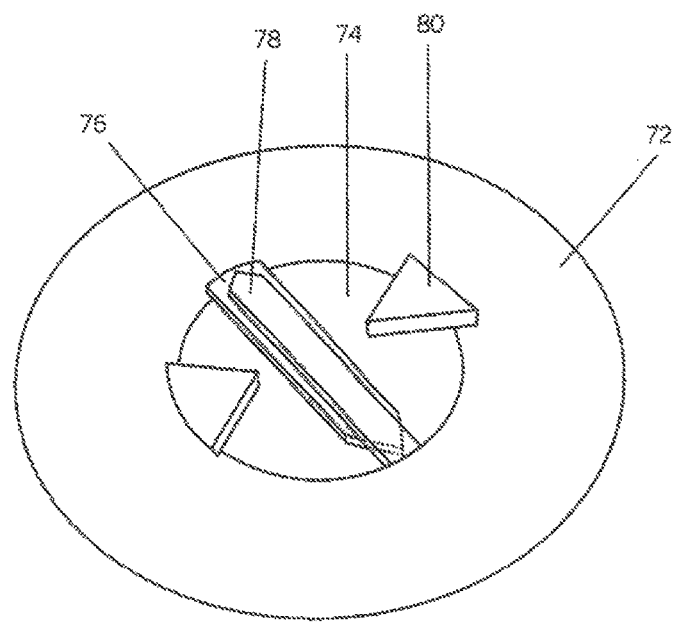

With more specificity and referring first to FIGS. 4, 5, and 7, a ring 70 with a toroidal ring body 72 defines a through-opening 74, and first and second axially rigid gripping members 76, 78 extend diametrically across the opening 56 one over the other, i.e., are offset from each other in the axial dimension defined by the body. That is, instead of being at the same location along the axis of the ring as in the previous embodiments, in FIGS. 4 and 5 the gripping members are at different locations along the axis. As was the case in the examples above, the gripping members 76, 78 shown in FIGS. 4, 5, and 7 each have a fixed end embedded in the body 72 and a free end that is disposed substantially diametrically across the through-opening 74 from the fixed end.

As perhaps best shown in FIG. 7, the first gripping member 76 is wider than the second gripping member 78, and the second gripping member 78 can lay flush against the first gripping member 76. In some examples, opposed short triangular stabilizing spikes 80 can have respective fixed ends embedded in the body 72 and respective pointed free ends closely juxtaposed with the gripping members 76, 78 near the center of the through-hole 74. The stabilizing spikes 80 are formed on the ring 70 in an orthogonal relationship to the gripping members 76, 78, extending into the through-opening 74.

Figure 8:
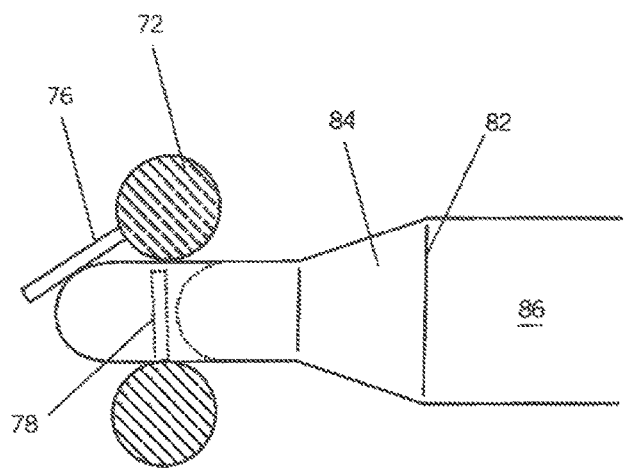

FIGS. 6-9 are now addressed to illustrate a specialized loading device 82 for loading the ring 70 for installation in a patient. Due to the overlapping gripping members 76, 78 interfering with each other in the resting condition shown in FIG. 7, the first member 76 is wider (or has some other distinguishing feature) than the second member 78 to facilitate a loading sequence. Specifically, note in cross-reference to FIGS. 8 and 9 that the loading device 82 is configured to engage and rotate the wider gripping member 76 out of the way first (FIG. 8, showing the first member 76 rotated out of the plane defined by the ring body 72), then the second, thinner gripping member 78 can be rotated (FIG. 9) outwardly from the plane of the body 72. The ring 70 is also expanded at the same time to be fitted on the delivery system as it rides up against a tapered portion 84 of the loading device 82, with the gripping members now rotated out of the plane of the ring such that they can ride against the device 82 until the body 72 is positioned on a larger cylindrical part 86 of the device 82 in an expanded (stretched) configuration.

Figure 9:
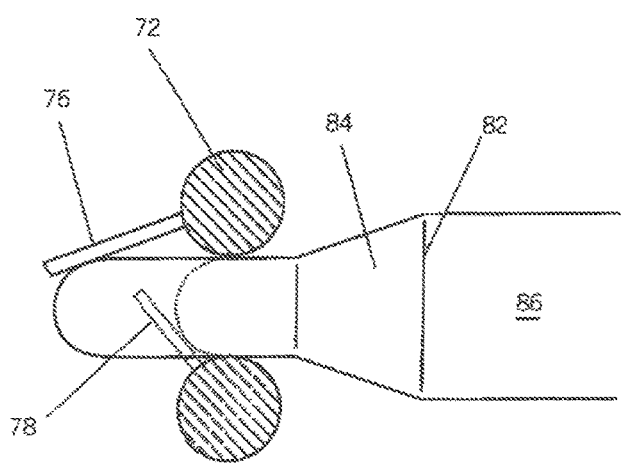

In one example, the device 82 may be formed with offset ramp portions arranged to engage the wider member 76 first and then engage the narrower member 78. In another example best illustrated in FIG. 6, the device 82 is formed with plural axially-oriented slots 88 that are wider than the second member 78 but narrower than the wider member 76. It will readily be appreciated that the distal end 90 of the device 82 will thus abut and push the wider member 76 as the ring 70 is slid proximally relative to the device 82 onto the device 82, while the narrower member 78 remains in the position shown in FIG. 8, riding through one of the slots 88. As the ring 70 is pushed further onto the device 82, eventually the narrower member 78 abuts a slot end 92. Continued relative motion from there causes the slot end 92 to push the narrower member 78 outwardly as shown in FIG. 9.

Figure 10A:
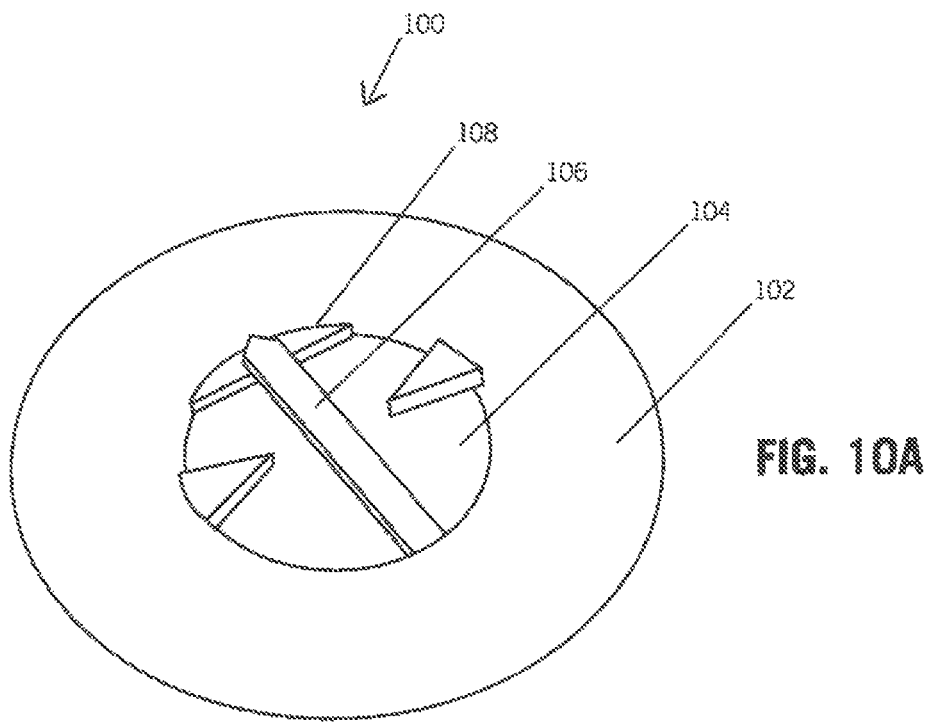
FIGS. 10A and 10B are a perspective and cross-sectional view, respectively, of a fifth embodiment of the ring.
Figure 10B:
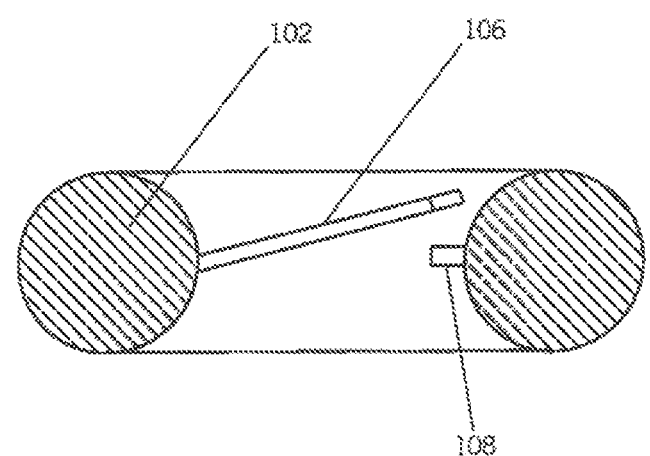
Figure 11:
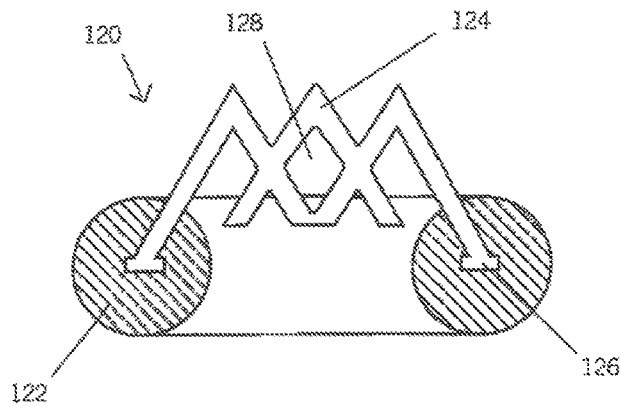
FIGS. 11-13D are views of a sixth embodiment of the ring.

Turning now to FIGS. 10A and 10B, a spike and tab configuration is shown. A ring 100 has a toroidal ring body 102 defining a through-opening 104, and a single axially rigid gripping member 106 extends diametrically across the opening 104. As shown, the gripping member 106 is long enough to reach across the diameter of the ring. The member 106 is also biased at an acute angle relative to the plane defined by the ring body 102 as shown in FIG. 11, and/or is curved so as it penetrates through the tissue, it always ends up on an outer side of a locking tab 108 which is embedded in the body 102 opposite to the fixed end of the member 106. Subsequently, any tissue movement trying to force the ring off will cause the free end of the elongated gripping member 106 to contact the tab 108 and thereby prevent any slippage of the ring off of the tissue.

Figure 12:
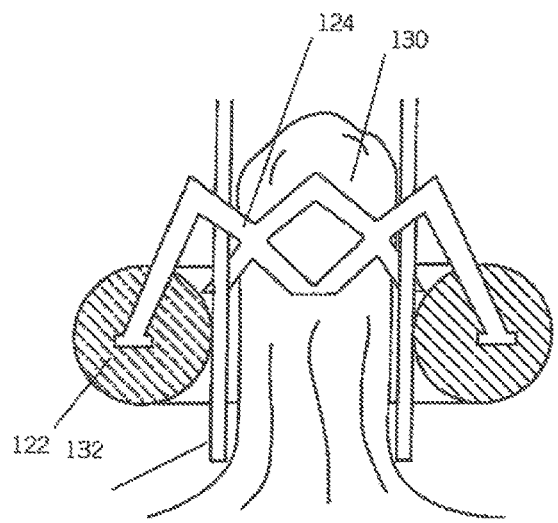

FIGS. 11-13 illustrate a toroidal ring 120 with a ring body 122 defining a through-opening in the manner of the devices disclosed above, except that in FIGS. 11-13 the through-opening is diametrically spanned by a flexible expandable cage structure 124 that is disposed in the through-opening as shown with opposed ends 126 embedded in the body 122. The cage structure 124 defines plural openings 128 into which tissue can extend and preferably has a central through-opening which can expand around the below-described delivery device. The webbed cage structure may be made similar to a stent using a laser to cut out portions of a tube such as but not limited to a nitinol tube, or it may be formed by arranging a wire into a cone-shaped structure. FIG. 13B shows the cage 131, which is tapered toward an apex and thus can be regarded as frusto-conical and in some cases completely conical, may also be formed by laser cutting or photoetching flat stock nitinol or steel and subsequently rolled to form the desired generally conical shape 133 shown in FIG. 13C. FIG. 13D shows silicone rubber is then overmolded onto the cage to form the body 122. The cage places the triangular spikes at a biased angle against the tissue. Stated differently, the spikes of the cage are oriented toward the long axis defined by the cage. Expulsion forces of the tissue causes these spikes to further engage the tissue and become tighter to prevent slippage of the ring.

Figure 13A:
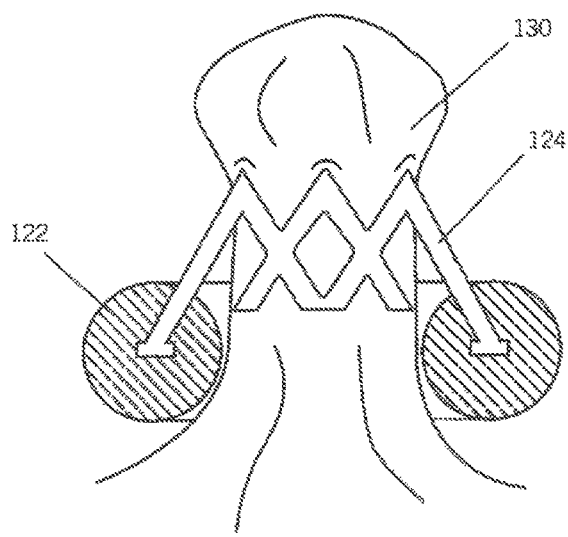
Figure 13B:
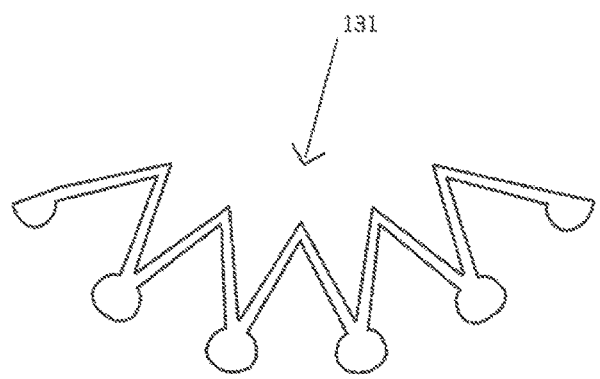
Figure 13C:
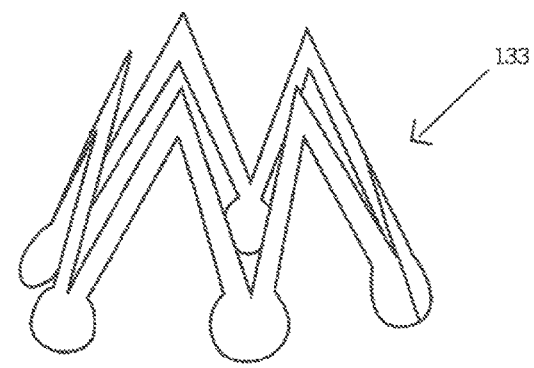
Figure 13D:
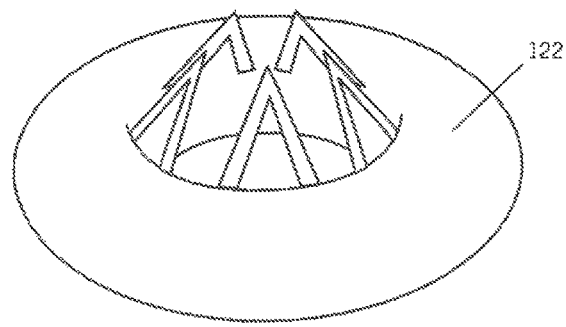

FIGS. 12 and 13A illustrate operational delivery of the ring 120 to constrict tissue 130. The ring 120 is stretched over a delivery device 132 in an expanded configuration shown in FIG. 12. The delivery device 132 is then removed while the ring 120 is held or remains in place to collapse around the tissue 130 as shown in FIG. 13A, constricting the tissue. The cage structure 124 grips and/or digs into the tissue 130 to prevent slippage of the ring 120 off of the tissue 130.

Figure 14A:
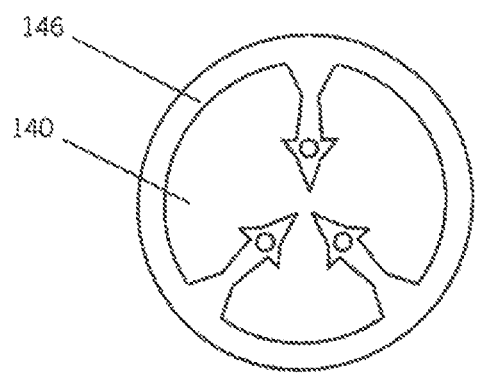
FIGS. 14A-C show three alternate spike configurations prior to manufacture.
Figure 14B:
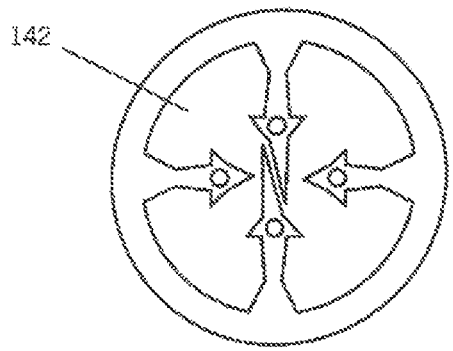
Figure 14C:
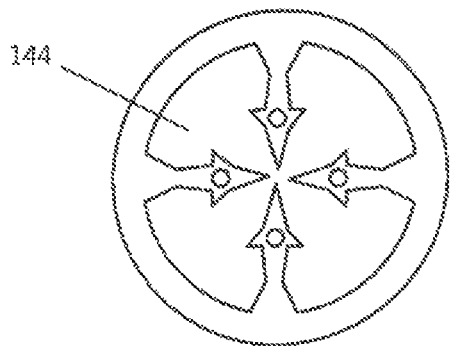

FIGS. 14A-C and 15A-D show manufacturing steps for making a ring such as any of the rings described above. As shown in FIGS. 14A-C various gripping member configurations may be used in addition to those described above. For example, as shown at 140 three gripping members may extend radially inwardly to almost meet each other, being radially spaced apart by 120°. Or, as shown at 142 and 144, four gripping members may be arranged at 90° intervals and can extend toward each other at a central point, with the ends of two opposed members slightly overlapping each other (142) or with the ends of all four members almost meeting each other at a central point (144).

Regardless of the particular gripping member configuration used, it will readily be appreciated in reference to FIGS. 14A-C that all gripping members have respective fixed ends arranged on a circular support 146, with the gripping members extending radially inward relative to the circular support 146. The circular support and gripping members are made of a unitary piece of material e.g., stainless steel, by, e.g., employing laser cutting or photoetching principles.

Figure 15A:
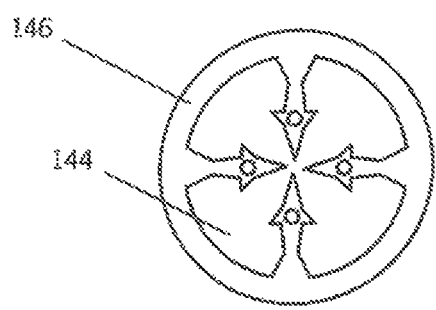
FIGS. 15A-D show a series of ring configurations during manufacturing to illustrate an example method for making a ring according to present principles.
Figure 15B:
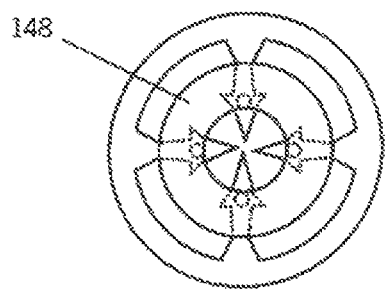
Figure 15C:
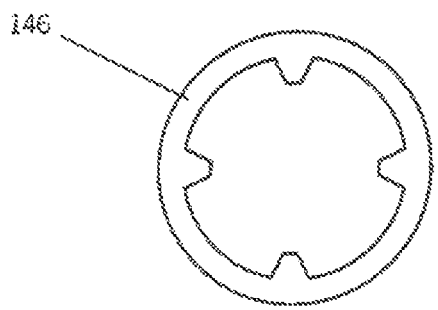
Figure 15D:
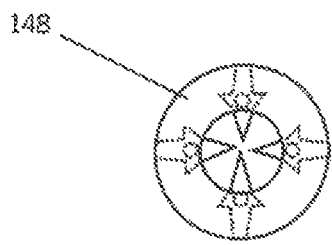
Figure 16:
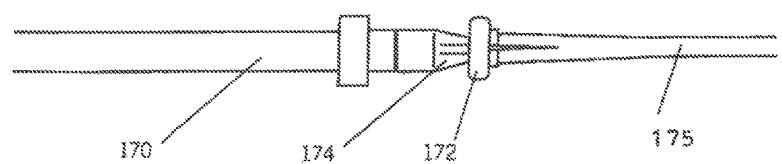
FIGS. 16-19 show various stages of loading the ring onto a delivery device.

Next, as shown in the illustration of FIG. 15B, a toroidal resilient ring 148 is overmolded onto the support/gripping member assembly. Thus, the support/gripping member assembly may be disposed in a mold having a toroidal cavity formed therein and then fluidic silicone rubber or other appropriate ring material injected into the cavity and heat cured to form the body 148. Then, as shown in FIGS. 15C and 15D, the gripping members and ring are removed from the circular support 146 to establish one of the present tissue gripping rings. Excess ring material may then be removed from the gripping members.

Referring briefly to FIG. 20, in one embodiment the overmolding step is executed in a mold 150 having first and second parts 152, 154 that when facing each other define a toroidal void into which material establishing the ring 148 is directed. The mold also is formed with spike channels into which the spikes or gripping members 156 are disposed prior to overmolding, with the circular support being sandwiched between the parts 152, 154. After molding, the first part 152 is distanced from the second part 154 to expose the ring 148 and spike 156.

In the example shown in FIG. 20, if desired ejector pins 160 may be provided in one of the parts of the mold. After distancing the first part 152 from the second part 154, the ring may be removed from the second part 154 by reciprocating the ejector pins 160 against the ring to push it out of the mold.

FIGS. 16-19 illustrate an assembly including a delivery device 170 onto which a ring 172 is to be disposed by pushing the ring 172 onto an expander tool 174 and then onto the delivery device 170, in some cases using an elongated axially rigid pusher tool 176. When disposed on the delivery device 170, the ring is stretched to a radially enlarged configuration such that when it is pushed off of the delivery device 170 onto tissue, the ring collapses to a relaxed, radially smaller configuration around the tissue.

Figure 17:
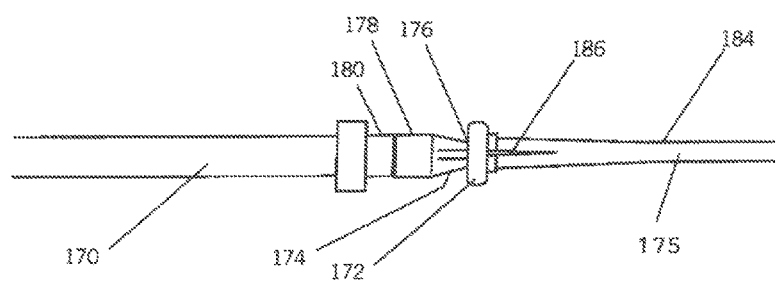
Figure 18:
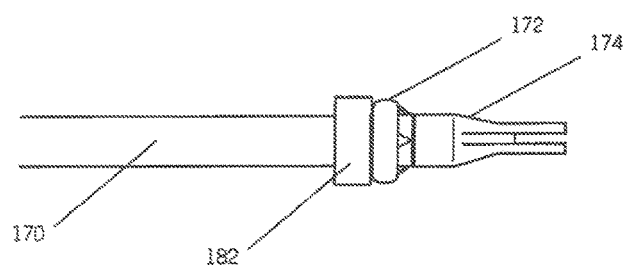

As best shown in FIG. 17, the expander 174 tapers radially outwardly from a first end 176 of the expander to a radially enlarged cylindrical segment 178, which has substantially the same diameter as the end segment 180 of the delivery device 170 onto which the ring 172 is to be disposed. In contrast, the diameter of the end 176 substantially equals the diameter of the ring 172 when the ring is in a relaxed state. As the ring 172 is pushed from the first end 176 toward the cylindrical segment 178, it expands, with the spikes being rotated out of the plane defined by the ring body as they ride against the tapered part of the expander 174.

Figure 19:
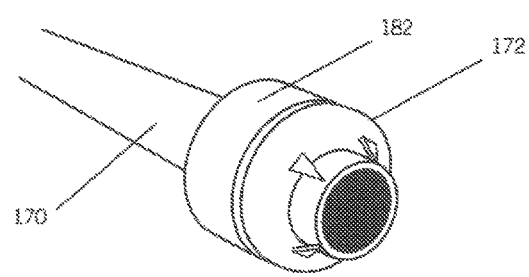

The cylindrical segment 178 of the expander 174 is juxtaposed with the carrying portion 180 of the delivery device 170 as shown, and then the ring 172 is pushed from the cylindrical segment 178 onto the carrying portion 180 (FIG. 18) to load die ring 172 in a stretched state for delivery to the tissue. The expander 174 is removed and the ring 172 is now loaded onto the delivery device 170 (FIG. 19). Subsequently, to push the ring 172 off of the delivery device, a collar 182 is moved against the ring to urge it off of the delivery device, either by pushing the collar 182 toward the ring or by retracting the carrying portion 180 toward the collar.

FIG. 17 perhaps best shows that when it is desired to push the ring onto the expander and delivery device using the pusher tool 176, the pusher tool 176 may be formed with an end segment 184 that in turn is formed with longitudinal slots 186. The slots 186 enable the end segment 184 to radially expand as the end segment 184 rides over the expander 174 from the first end 176 of the expander toward the cylindrical portion 178 of the expander.

While the particular DEVICES AND METHODS FOR SECURING TISSUE are herein shown and described in detail, it is to be understood that the subject matter which is encompassed by the present invention is limited only by the claims.

What is claimed is:

1. Method for configuring a resilient ring for placement in a patient to cause the ring to surroundingly grip tissue in the patient, comprising:

engaging the ring with a first end of an expander, the expander tapering radially outwardly from the first end to a cylindrical segment, a diameter of the first end substantially equaling a diameter of the ring when the ring is in a relaxed state;

pushing the ring along the expander to radially stretch the ring until the ring surrounds the cylindrical segment, wherein the act of pushing is executed using an elongated axially rigid pusher tool, the pusher tool having an end segment formed with longitudinal slots to enable the end segment to radially expand as the end segment rides over the expander from the first end of the expander toward the cylindrical segment of the expander, the longitudinal slots extending longitudinally in a direction parallel to the direction the ring is pushed;

juxtaposing the cylindrical segment with a carrying portion of delivery device having substantially the same diameter as the cylindrical segment; and pushing the ring from the cylindrical segment onto the carrying portion to load the ring in a stretched state for delivery to the tissue.

2. The method of claim 1, wherein the delivery device includes a pushing collar having a larger radius than the ring when in the stretched state, the pushing collar being axially movable relative to the ring to push the ring off the carrying portion onto the tissue.

* * * * *